United States Patent [19]

Andrianov et al.

[11] Patent Number: 5,807,757

[45] Date of Patent: Sep. 15, 1998

[54] PREPARATION OF IONICALLY CROSS-LINKED POLYPHOSPHAZENE MICROSPHERESY BY COACERVATION

[75] Inventors: Alexander K. Andrianov, Belmont; Jianping Chen, Lexington, both of Mass.

[73] Assignee: Virus Research Institute, Inc., Cambridge, Mass.

[21] Appl. No.: 675,713

[22] Filed: Jul. 2, 1996

[51] Int. Cl.$^6$ .................. G01N 33/544; A01N 63/00; C12N 11/04

[52] U.S. Cl. .................. 436/535; 424/204.1; 424/208.1; 424/212.1; 424/215.1; 424/217.1; 424/219.1; 424/226.1; 424/227.1; 424/229.1; 424/245.1; 424/247.1; 424/249.1; 424/286.1; 424/93.1; 424/93.4; 424/93.41; 435/182; 428/402.24; 530/817

[58] Field of Search .................. 435/174, 177, 435/180, 182; 558/157; 428/402.2, 403; 424/204.1, 208.1, 212.1, 215.1, 217.1, 219.1, 226.1, 227.1, 229.1, 245.1, 247.1, 249.1, 286.1, 93.1, 93.4, 93.41; 530/817; 436/535

[56] References Cited

U.S. PATENT DOCUMENTS

| | | | |
|---|---|---|---|
| 4,622,244 | 11/1986 | Lapka et al. | 427/213.32 |
| 4,880,622 | 11/1989 | Allcock et al. | 424/78 |
| 4,948,586 | 8/1990 | Bohm et al. | 424/406 |
| 5,053,451 | 10/1991 | Allcock et al. | 524/600 |
| 5,149,543 | 9/1992 | Cohen et al. | 424/499 |
| 5,529,777 | 6/1996 | Andrianov et al. | 424/184.1 |
| 5,562,099 | 10/1996 | Cohen et al. | 428/662.02 |

FOREIGN PATENT DOCUMENTS

WO95/02416  1/1995  WIPO .

OTHER PUBLICATIONS

Deasy, *Drugs and the Pharmaceutical Sciences*, vol. 20, Microencapsulation and Related Drug Processes, Marcel Dekker, Inc., New York, pp. 61–95 (1984).

Allcock, et al., *Macromolecules*, vol. 22, pp. 75–79 (1989).

Bano, et al., *Biotechnology*, vol. 9, pp. 468–471 (May 1991).

Axelos, et al., *Macromolecules*, vol. 27, pp. 6594–6602 (1994).

Payne, et al., *Advances in Mucosal Immunology*, Mestecky, et al., eds., Plenum Press, New York, pp. 1475–1480 (1995).

*Primary Examiner*—David M. Naff
*Attorney, Agent, or Firm*—Elliot M. Olstein; Raymond J. Lillie

[57] ABSTRACT

A method is provided for preparing polyphosphazene microspheres wherein the polyphosphazene microspheres are produced by coacervation. A solution containing a polyphosphazene is admixed with a solution containing a salt of a monovalent ion such as a salt of a Group I element (for example, NaCl) to form a dispersion containing polyphosphazene coacervate microdroplets. The dispersion then is admixed with a solution containing a salt of a multivalent ion, such as a salt of a Group II element (for example, $CaCl_2$) to form a suspension of polyphosphazene microspheres. The polyphosphazene microspheres then are recovered from the suspension. Such method enables one to obtain high yields of microspheres having a controlled size distribution. Polyphosphazene microspheres containing biological material can be produced by providing a biological material in the polyphosphazene solution that is mixed with the solution containing a salt of a monovalent ion. The biological material may be an antigen or other biological material selected from proteins, nucleic acids, polysaccharides and synthetic compounds having biological activity.

24 Claims, 6 Drawing Sheets

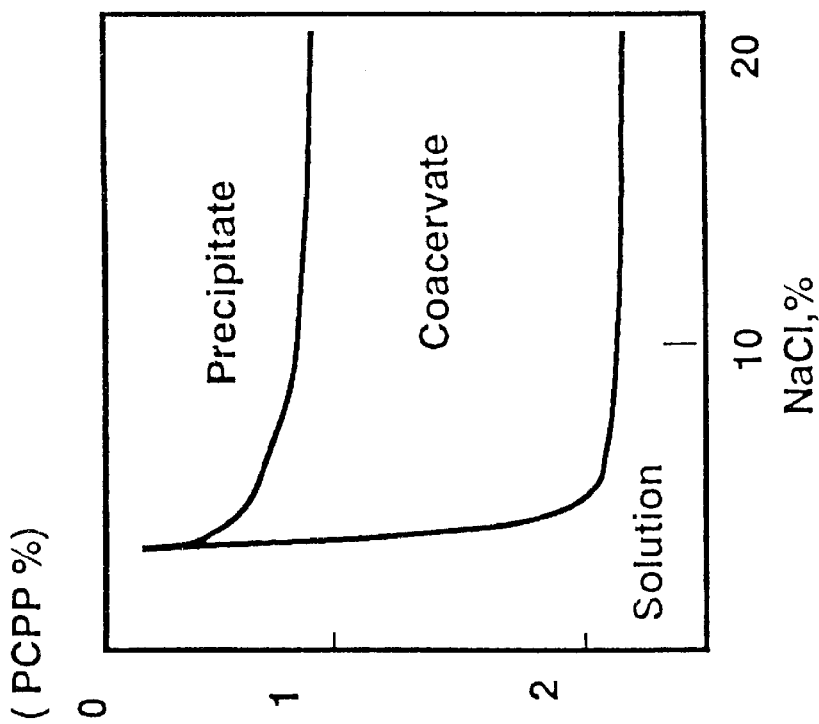
F I G. 1
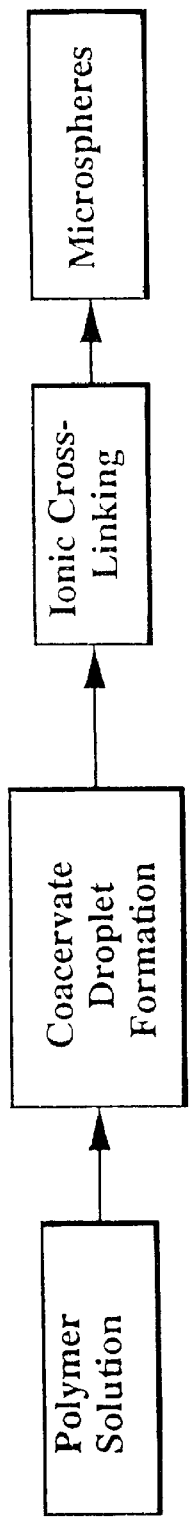
F I G. 2

PREPARATION OF IONICALLY CROSS-LINKED POLYPHOSPHAZENE MICROSPHERESY BY COACERVATION

BACKGROUND OF THE INVENTION

This invention relates to the preparation of polyphosphazene microspheres. More particularly, this invention relates to the preparation of polyphosphazene microspheres by coacervation of the polyphosphazene.

Water soluble polymers and polymeric hydrogels, such as polyphosphazene hydrogels, may be used to microencapsulate antigens for delivery to mucosal surfaces and for the controlled release of antigen at the mucosal surface, or for injection. Such encapsulated antigen also may be administered orally or intranasally.

Polyphosphazene microspheres may be employed as pharmaceutical carriers for a variety of prophylactic and/or therapeutic agents. For example, polyphosphazene microspheres may serve as immunoadjuvants, whereby such microspheres may contain any of a variety of antigens, such as antigens which may be derived from cells, bacteria, virus particles, or portions thereof, the antigen may be a protein, peptide, polysaccharide, glycoprotein, glycolipid, nucleic acid, or combination thereof, which elicits an immunogenic response in an animal, for example, a mammal, bird, or fish.

In general, the encapsulated antigen may be mixed with a polyphosphazene solution, microparticles of the polyphosphazene and antigen are formed, and the polyphosphazene is crosslinked ionically or covalently to form a stable biodegradable microparticle. The microparticles adhere to mucosal surfaces such as the mucosal lining of the gastrointestinal tract, increasing takeup by the reticuloendothelium of antigen as it is released over time. The polyphosphazene may be cross-linked ionically with a polyion or divalent cation, such as calcium chloride.

Methods for preparation of synthetic polymer microspheres including polyelectrolyte hydrogel microspheres have been described; however, these methods require the use of organic solvents and surfactants. Examples of such methods are described in U.S. Pat. No. 4,948,586, issued to Bohm, et al.

Hydrogel microspheres or nanoparticles can be prepared in aqueous solutions by a simple coacervation process using natural polyelectrolytes, such as gelatin and some synthetic polyelectrolytes. High concentrations of salt or elevated temperatures were used to induce coacervate formation. Microsphere preparation according to these methods, however, requires the use of a water-insoluble "core" material in a liquid or solid form, such as oils, parafin or water-insoluble drugs. (Deasy, et al., *Microencapsulation and Related Drug Processes,* Marcel Dekker, Inc., New York, pgs. 61–95 (1984); U.S. Pat. No. 4,622,244, issued to Lapka, et al.) The polymer-rich coacervate droplets deposit on the surface of dispersed water-insoluble core material and then coalesce to form the coating which is usually then cross-linked by chemical means.

U.S. Pat. No. 5,149,543, issued to Cohen, et al., teachaes that ionically cross-linked polyphosphazene hydrogel microspheres can be prepared by spraying an aqueous polyphosphazene solution into a solution containing multivalent cations. This method then was modified to produce microspheres in a micron size range. (Payne, et al., *Advances in Mucosal Immunology,* Mestecky, et al., eds. Plenum Press, New York, pgs. 1475–1480 (1995).) This process, however, requires complicated spraying equipment, and it is difficult to control the microsphere size distribution, especially to achieve high yield and narrow size distribution of microspheres having sizes in the micron range.

The Cohen, et al. patent also teaches that ionically cross-linked polyphosphazene hydrogel microspheres are unstable in the presence of monovalent ions and their treatment with excess aqueous potassium chloride at pH 7.5 results in cleavage of the ionic cross-links. Disintegration of microspheres in phosphate buffered saline (pH 7.4) was also observed. (Bano, et al., *Bio Technology,* Vol. 9, pgs. 468–471 (1991).) Allcock, et al., U.S. Pat. No. 5,053,451, also teach cleavage of ionic cross-links in the presence of KCl. Axelos, et al., *Macromolecules,* Vol. 27, No. 22, pgs. 6594–6602 (1995) demonstrate that a monovalent salt, such as sodium chloride, dissolves or precipitates hydrogels formed by ionic cross-linking of polyelectrolyte with divalent metals.

It is therefore an object of the present invention to provide a method of producing ionically cross-linked polyphosphazene hydrogel microspheres with a controlled microsphere size distribution without the use of elevated temperatures, organic solvents, water-insoluble core materials, or complex manufacturing equipment. In such a method, a solution containing a polyphosphazene is subjected to aqueous coacervation using a salt of a monovalent ion.

It is a further object of the present invention to provide a method for encapsulating biological materials by mixing biological material with either polyphosphazene solution before microsphere preparation, or with prepared polyphosphazene microspheres.

In accordance with an aspect of the present invention, there is provided a method of producing polyphosphazene microspheres. In such method, a solution containing a polyphosphazene is subjected to coacervation.

The term "coacervation" as used herein means the separation of a macromolecular solution into two immiscible liquid phases. One phase is a dense coacervate phase, concentrated in the macromolecules, and the other phase is a polymer deficient phase. Coacervation is a result of a molecular dehydration of the polymer and may be induced by a temperature change, the addition of a non-solvent, or the addition of a micro-salt (simple coacervation), or may be induced by the addition of another polymer to form an interpolymer complex (complex coacervation).

Coacervates may be described as liquid crystals and mesaphases and are more fluid than other systems with higher structural order, such as micelles. Such systems are in dynamic equilibrium and changes in the conditions may result in either the reformation of a one-phase system or the formation of a flocculate or precipitate. (Burgess, *Macromolecular Complexes in Chemistry and Biology,* Dubin, et al., eds., Springer-Verlag, Berlin, pgs. 285–300 (1994).)

The advantages of the method for making microspheres using coacervation are that it avoids the use of organic solvents, heat, complicated manufacturing equipment, such as spray equipment and eliminates generation of the aerosol. The method is highly reproducible and generates microspheres with an improved, more narrow microsphere size distribution, compared to the spray technique. Contrary to the microspheres obtained by spray method, coacervation microspheres do not contain significant amount of larger size aggregates or amorphous precipitate. This result is important for the preparation of microspheres for vaccine delivery since the uptake of these microspheres by M-cells is limited to the particles having diameter of 10 $\mu$m or less (Payne, et al., 1995). A further advantage of the coacervation process that it enables the efficient control of the microsphere size by simply varying the concentration of the components.

SUMMARY OF THE INVENTION

In one embodiment, the polyphosphazene microspheres are produced by admixing a solution containing polyphosphazene polyelectrolyte with a solution containing a salt of a monovalent ion to form coacervate droplets. The dispersion then is admixed with a solution containing a salt of a multivalent ion, whereby the microspheres are stabilized. If desired, the polyphosphazene microspheres then are recovered from the dispersion.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

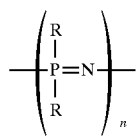

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino, including alkylamino-, heteroaralkyl, di (aliphatic) amino- including dialkylamino-, arylamino-, diarylamino-, alkylarylamino-, -oxyaryl including but not limited to -oxyphenylCO$_2$H, -oxyphenylSO$_3$H, -oxyphenylhydroxyl and -oxyphenylPO3H; -oxyaliphatic including -oxyalkyl, -oxy(aliphatic)CO$_2$H, -oxy(aliphatic) SO$_3$H, -oxy(aliphatic)PO$_3$H, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, -thioaralkyl, —NHC(O)O— (aryl or aliphatic), —O—[(CH$_2$)$_x$O]$_y$—CH$_2$)—O—[(CH$_2$)$_x$O]$_y$(CH$_2$)$_x$NH(CH$_2$)$_x$SO$_3$H, and —O—[(CH$_2$)$_x$O]$_y$—(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

Phosphazene polyelectrolytes are defined herein as polyphosphazenes that contain ionized or ionizable pendant groups that render the polyphosphazene anionic, cationic or amphiphilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte is a polyanion and contains pendant groups that include carboxylic acid, sulfonic acid, hydroxyl, or phosphate moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

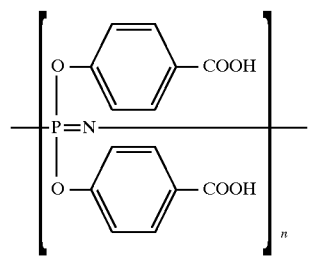

wherein n is an integer, preferably an integer between 10 and 300,000, and preferably between 1,000 to 300,000. This polymer has the chemical name poly [di (carboxylatophenoxy) phosphazene] or, alternatively, poly [bis(carboxylatophenoxy)phosphazene] (PCPP).

The phosphazene polyelectrolyte is preferably biodegradable to prevent eventual deposition and accumulation of polymer molecules at distant sites in the body, such as the spleen. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C.

Polyphosphazenes, including phosphazene polyelectrolytes, can be prepared by a macromolecular nucleophilic substitution reaction of poly(dichloro phosphazene) with a wide range of chemical reagents or mixture of reagents in accordance with methods known to those skilled in the art. Preferably, the phosphazene polyelectrolytes are made by reacting the poly(dichloro phosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly (dichlorophosphazene) and the reaction conditions as necessary. Preferred polyphosphazenes have a molecular weight of over 1,000, more preferably from about 500,000 to about 1,500,000.

The polyphosphazene may be contained in an appropriate solution, such as, for example, phosphate buffered saline (PBS), inorganic or organic buffer solutions, or aqueous solutions of biological materials, such as proteins, antigens, or mixtures thereof. The polyphosphazene may be present in the solution at any concentration, pH, and ionic strength, preferably at a concentration of from about 0.01% to about 1.5%, and a pH from 7 to 8.

The polyphosphazene solution is admixed with a solution containing at least one salt of a monovalent ion, such as a salt of a Group I element, such as a sodium or lithium salt. Other salts of monovalent ions which may be employed include, but are not limited to, ammonium salts. In one embodiment, the salt of a monovalent ion is a salt of a Group I element. Preferably, the salt of a Group I element is a sodium salt, such as sodium chloride, sodium sulfate, or sodium phosphate. Preferably, the sodium salt is sodium chloride, or NaCll. The salt of the monovalent ion may be present in the solution at any concentration and pH, preferably at a concentration of from about 0.1% to about 40% and a pH from 7 to 8.

The resulting mixture of the polyphosphazene solution and the solution including a salt of a monovalent ion is allowed to stand for a period of time which is sufficient to allow the formation of a coacervate phase; i.e., coacervate microdroplets of polyphosphazene are formed in the mixture. After a significant amount of microdroplets have been formed in the mixture, the mixture is added to a solution including at least one salt of a multivalent ion, such as zinc, calcium, bismuth, barium, magnesium, aluminum, copper, cobalt, nickel, or cadmium. In one embodiment, the salt of the monovalent ion is a calcium salt, such as calcium chloride, calcium bromide or calcium acetate. Preferably, the calcium salt is calcium chloride, or $CaCl_2$. The salt of the multivalent ion may be present in the solution at any concentration and pH, preferably from about 1% to about 25% and a pH from 7 to 8. The $Ca^{2+}$ ions in the solution serve as a cross-linker, whereby the microspheres are stabilized when they contact the solution containing the calcium salt.

The suspension of the polyphosphazene microspheres in the resulting solution which includes a salt of a monovalent ion and a salt of a multivalent ion is stirred for a period of time sufficient to form a suspension of stabilized microspheres. If desired, the microspheres then may be recovered from the suspension by means known to those skilled in the art, such as, for example, by centrifugation.

In another embodiment, the microspheres may be formed by preparing a water soluble interpolymer complex of a polyphosphazene and another water soluble polymer that can form a water-soluble interpolymer complex by means of electrostatic, hydrogen, or hydrophobic interactions. In one embodiment such a polymer is a poly (ethylene oxide-propylene oxide). The interpolymer complex can be formed at any molecular ratio which does not cause precipitation, any pH, any ionic strength, and any temperature, preferably at a pH from 7 to 8 and at room temperature. Induction of coacervation then is effected by the addition of a solution of a salt of a monovalent ion, such as hereinabove described to form interpolymer complex coacervate droplets. The microdroplets then may be stabilized by adding the dispersion containing the microspheres to a solution containing a salt of a multivalent ion as hereinabove described.

The preparation of polyphosphazene microspheres by coacervation enables one to recover an increased yield of polyphosphazene microspheres having a size in the micron range (up to 90 differential percent by volume and 95 differential percent by number), and produce microspheres of other sizes if needed without the use of elaborate equipment.

The microspheres, formed by coacervation, as hereinabove described, may be employed as carriers for a variety of prophylactic or therapeutic agents. In one embodiment, the microspheres may be employed as carriers of a biological material such as an antigen, which is capable of eliciting an immune response in an animal. The antigen may be derived from a cell, bacterium, virus particle, or a portion thereof. The antigen may be a protein, peptide, polysaccharide, glycoprotein, glycolipid, nucleic acid, or a combination thereof, which elicits an immune response in an animal, including mammals, birds, and fish. The immune response may be a humoral immune response or a cell-mediated immune response. In the event the material to which the immune response is to be directed is poorly antigenic, it may be conjugated to a carrier such as albumin or to a hapten, using standard covalent binding techniques, for example, with one of the several commercially available reagent kits.

In one embodiment, the microsphere is employed to deliver a nucleic acid sequence which encodes an antigen to a mucosal surface where the nucleic acid is expressed.

Particular examples of antigens which may be contained in the polyphosphazene microspheres include, but are not limited to, viral proteins such as influenza proteins, human immunodeficiency virus (HIV) proteins, Herpes virus proteins, and hepatitis A and B proteins, and antigens derived from rotavirus, measles, mumps, rubella, and polio; and bacterial proteins and lipopolysaccharides such as Gram-negative bacterial cell walls, and antigens derived from organisms such as Haemophilus influenza, Clostridium tetani, Corynebacterium diphtheria, and Neisseria gonhorrhoae.

In general, the antigen is mixed with the polymer solution prior to coacervation to insure dispersion of the antigen throughout the microsphere.

The microspheres, which contain an antigen, can be administered as a vaccine by any method known to those skilled in the art that elicits an immune response, including parenterally (intravenously, intramuscularly, subcutaneously, intraperitoneally, etc.), orally, or by transmembrane or transmucosal administration. Preferably, the vaccine is administered transmucosally. Nonlimiting examples of routes of delivery to mucosal surfaces are intranasal (or generally, the nasal associated lymphoid tissue), respiratory, vaginal, and rectal.

The dosage is determined by the antigen loading and by standard techniques for determining dosage and schedules for administration for each antigen, based on titer of antibody elicited by the microsphere antigen administration.

BRIEF DESCRIPTION OF THE DRAWINGS

The invention now will be described with respect to the drawings, wherein:

FIG. 1 is a phase diagram for a coacervation system formed by mixing solutions of PCPP and sodium chloride, wherein the concentration of NaCl is plotted against polymer concentration;

FIG. 2 is a schematic of the preparation of polyphosphazene microspheres;

DETAILED DESCRIPTION OF THE INVENTION

The invention now will be described with respect to the following examples; however, the scope of the present invention is not intended to be limited thereby.

EXAMPLE 1

Preparation of polyphosphazene coacervate droplets.

The ability of aqueous polyphosphazene solutions to form coacervate systems was demonstrated using PCPP and sodium chloride. PCPP (molecular weight $10^6$ g/mol) was dissolved in an equivalent amount of 0.25% sodium hydroxide solution and then diluted with deionized water to prepare solutions in the range of concentration 0.01%–1.11% (pH 7.4). Sodium chloride solutions in water were also prepared in the range of concentration 2–30%. Polymer solutions then were mixed with sodium chloride solutions in the ratio 0.4 ml : 0.74 ml and agitated by shaking. The solutions or dispersions were examined by microscope to determine the presence of coacervate droplets or precipitate. A phase diagram was then established by plotting the concentration of NaCl in the mixture against polymer concentration (FIG. 1). The diagram contains three major regions—coacervate, precipitate, and homogeneous solution.

EXAMPLE 2

Preparation of ionically cross-linked polyphosphazene microspheres.

Figure 3A:
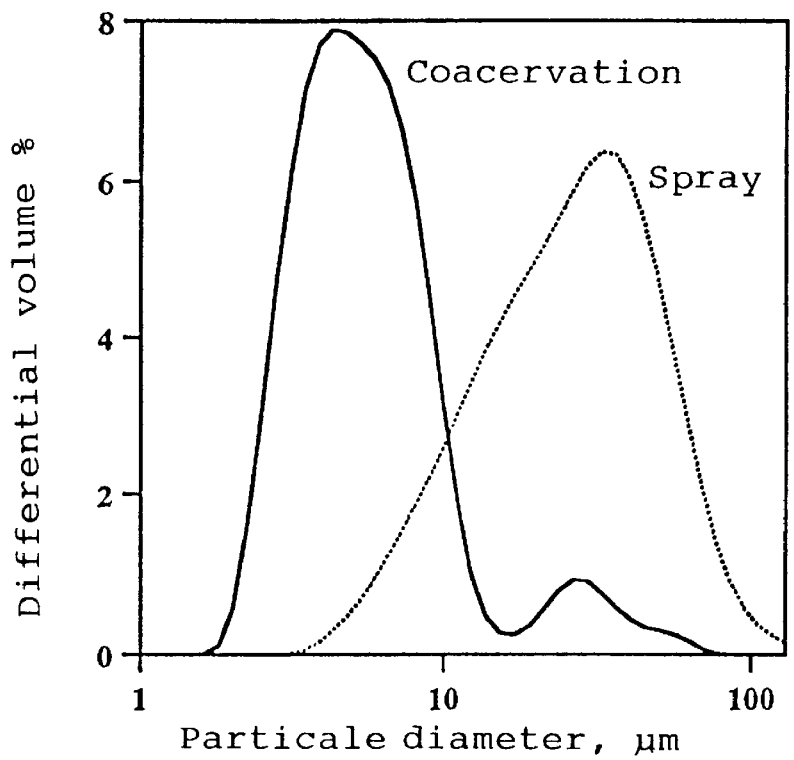
FIG. 3 is a graph of the differential percentage of microsphere diameters by volume and by number, as prepared by coacervation and spray methods.
Figure 3B:
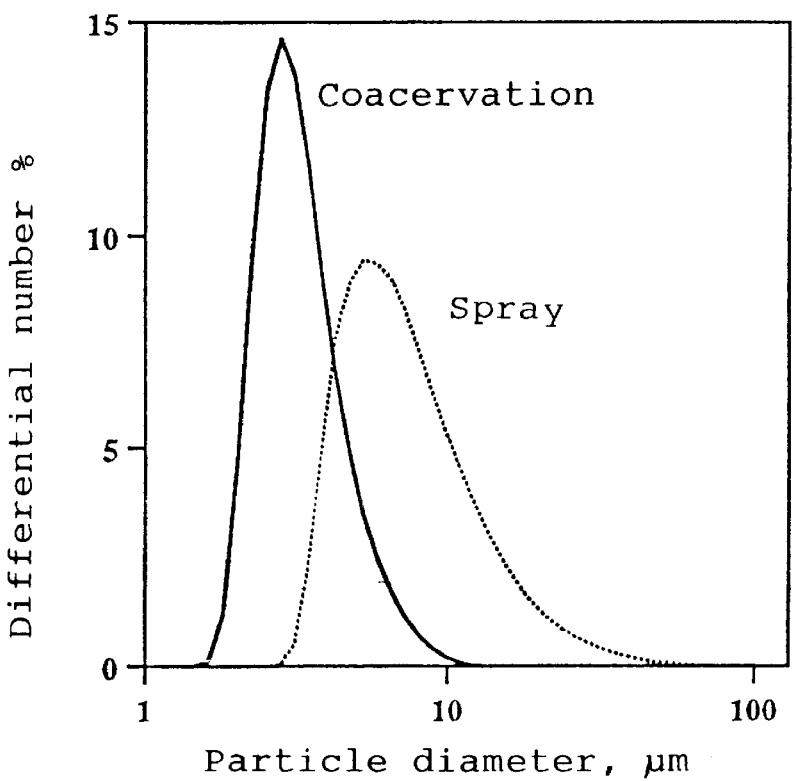
Figure 4:
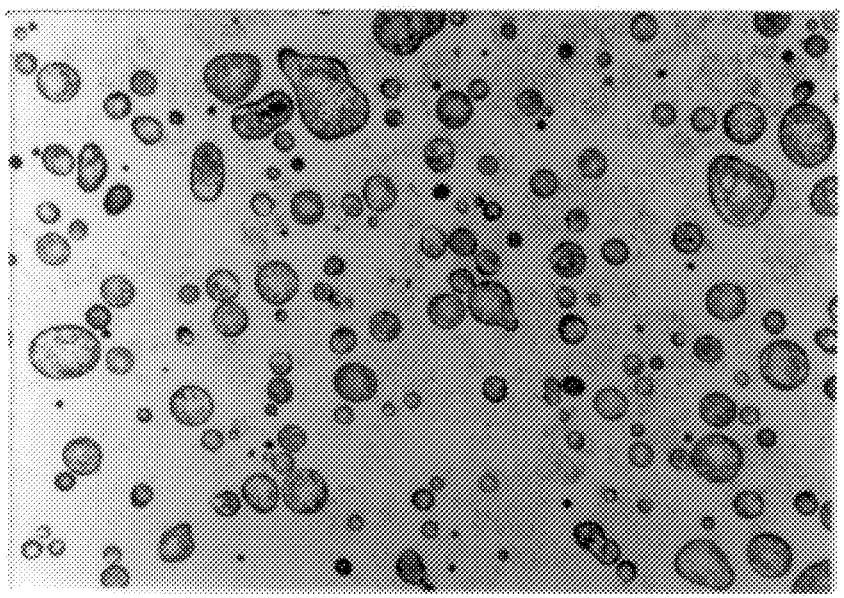
FIG. 4 is an electron micrograph of ionically cross-linked PCPP microspheres prepared by a coacervation method.

Ionically cross-linked microspheres of PCPP were prepared by first coacervating an aqueous polyphosphazene solution with a solution of sodium chloride in water and then by treating the resulting mixture with an aqueous solution of calcium chloride as shown in FIG. 2. 4 ml of 0.2% solution of PCPP (molecular weight—$1.1 \times 10^6$ g/mol) in PBS and 7.4 ml of 6.2% sodium chloride solution in water were mixed, shaken and incubated at room temperature for 6 minutes or until coacervate droplets with a mean size approximately 4–6 $\mu$m were formed. The obtained coacervate dispersion then was poured in 800 ml of 8.8% calcium chloride solution in water. The suspension was stirred using a magnetic stirrer for 20 minutes and then the microspheres were isolated by centrifugation (300 rpm, 10 min.) Microspheres were washed with deionized water, collected by centrifugation under the same conditions, and stored at room temperature. Obtained microspheres had a spherical shape when examined in the optical microscope and no amorphous precipitate was detected. Particle size distribution by number and by weight was analyzed by a Coulter LS 100 Particle Sizer and demonstrated narrow particle size distribution. The percentage of microspheres under 10 $\mu$m is 90% (by volume) and 99.7% (by number) (FIG. 3). Electron microphotographs of dried microspheres also revealed homogeneous size distribution and spherical shape of the microspheres (FIG. 4).

In a comparative experiment, 2.5% solution of PCPP in PBS was pumped into an ultrasonic spray nozzle (Medsonic, Inc., Farmingdale, N.Y.) under 35 pounds per square inch of sterile air, resulting in the generation of a microdroplet spray that impacts a 7.5% calcium chloride solution where the microdroplets are cross-linked by the calcium to form microspheres. Microspheres were incubated in calcium chloride solution for 30 minutes, collected by centrifugation (2600 rpm, 15 min.), washed with deionized water and collected by centrifugation under the same conditions. Microscopic observations revealed the presence of spherical microspheres together with some irregularly shaped amorphous polymer aggregates. These results are confirmed by the analysis of the microsphere dispersion by a Coulter LS Particle Sizer. Although the differential percentage of microspheres by number in the size range 1–10 $\mu$m is relatively high (75%), the percentage of microspheres in the same size range calculated by volume is low (10%) indicating the presence of large particles (FIG. 3). These particles are visually detectable as an amorphous precipitate under, examination in an optical microscope. Changes in the parameters, such as concentration of PCPP and air pressure typically resulted in the formation of larger quantities of amorphous aggregates without significant changes in the size of microspheres.

Thus the use of a coacervation process for microsphere preparation results in the production of microspheres of narrow size distribution without formation of amorphous aggregates. Previous work has shown that uptake of particulate material by M-cells is limited to particles having diameter of 10 $\mu$m or less (Payne, et al., 1995), which makes microsphere size distribution critical for the preparation of effective vaccine delivery vehicles. Thus the increase in the percentage of the microspheres with a size under 10 $\mu$m by volume from 10% for spray method to 90% for coacervation results in the significant increase of the material that can be actually delivered to the target cells.

EXAMPLE 3

Preparation of ionically cross-linked polyphosphazene microspheres of variable sizes.

Figure 5:
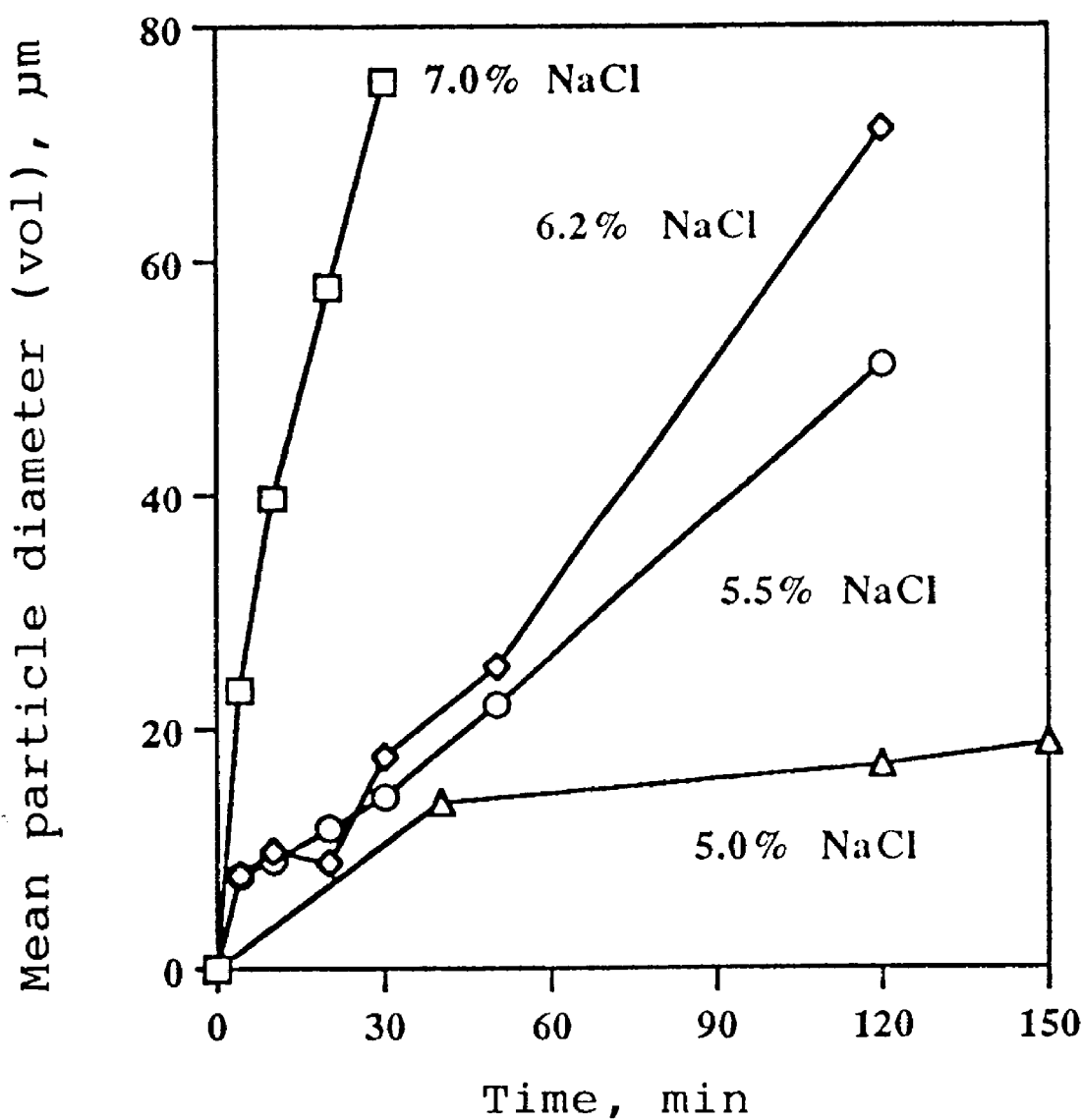
FIG. 5 is a graph of the mean particle size diameter of the ionically cross-linked PCPP microspheres over time of coacervate droplet incubation in NaCl for different salt concentrations.

The effect of sodium chloride concentration and incubation time with sodium chloride on the size of ionically cross-linked PCPP microspheres was investigated. A series of 0.2% PCPP (molecular weight—$1.1 \times 10^6$ g/mol) solutions were prepared and then coacervated with 6.2% aqueous solution of sodium chloride in a ratio 0.4 ml: 0.74 ml. The coacervation process was then stopped at different time points by cross-linking of polymer microdroplets with 400 ml of 8.8% calcium chloride, microspheres were isolated and analyzed on a particle sizer as described in Example 2. The mean diameter of obtained microspheres was then plotted against incubation time in sodium chloride (FIG. 5). Kinetic curves obtained for different concentrations of sodium chloride (4%, 5.5% and 7%) are also shown in FIG. 5. No formation of amorphous precipitate was detected by microscopic observations under these conditions. The results indicate that the microsphere size can be controlled efficiently by varying concentrations of sodium chloride and incubation times.

EXAMPLE 4

The effect of calcium chloride concentration.

Figure 6A:
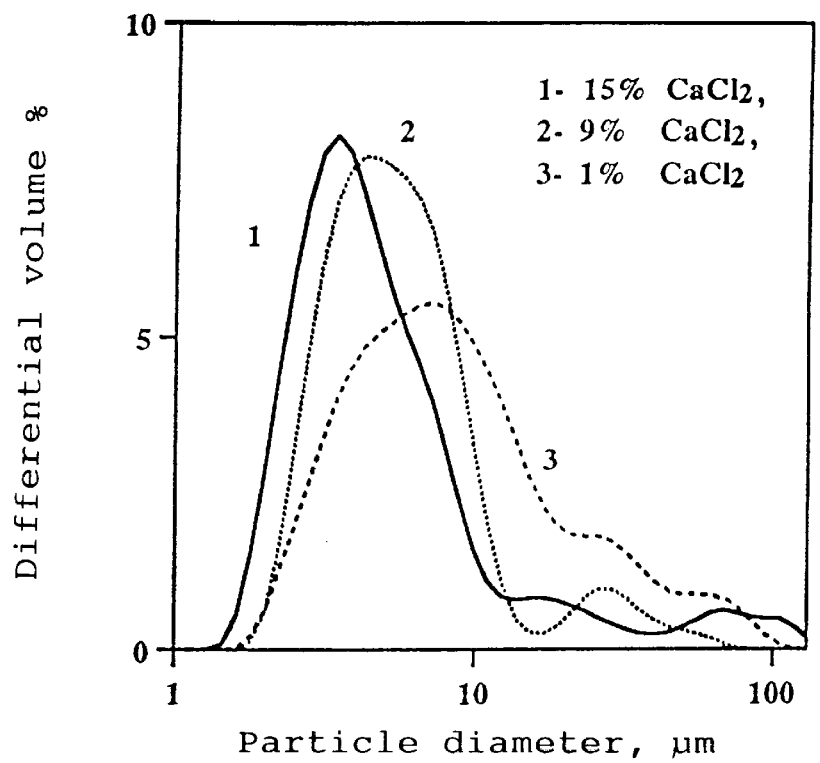
FIG. 6 is a graph of the differential percentages of microspheres by volume and by number for ionically cross-linked PCPP microspheres prepared with different concentrations of $CaCl_2$.
Figure 6B:
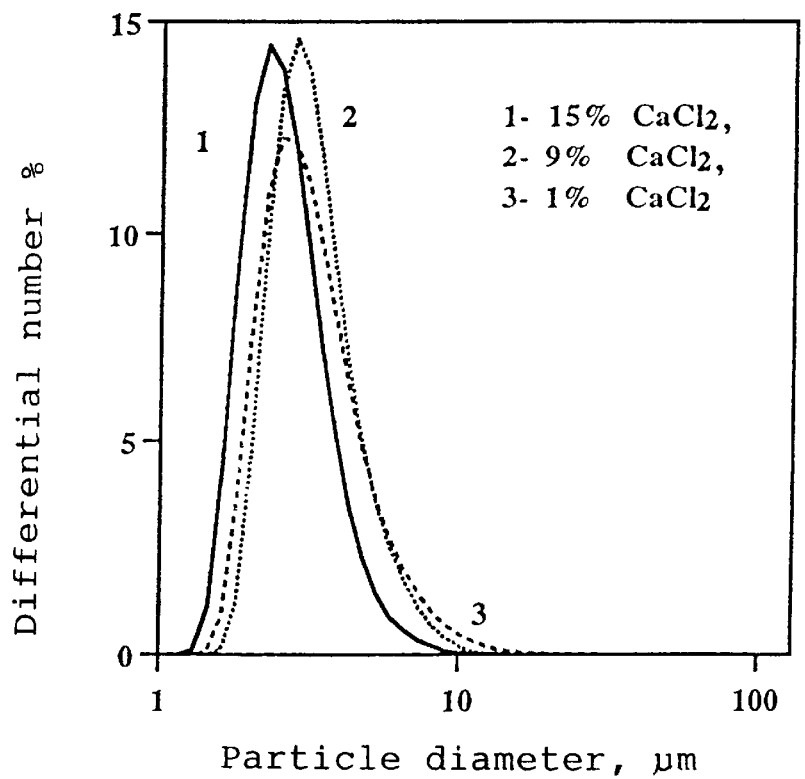

The effect of calcium chloride concentration on the microsphere size distribution was studied using the same conditions for coacervate preparation as in Example 3, except only one sodium chloride solution with concentration 6.2% was used. Coacervate systems were crosslinked by mixing with 400 ml of calcium chloride solutions of different concentrations (1%, 9% and 15%) for 6 minutes. Microspheres were separated and their size distribution was analyzed as described in Example 3. The results (FIG. 6) show that a wide range of calcium chloride concentrations can be used to prepare microspheres without affecting their size.

EXAMPLE 5

The effect of polymer concentration.

Figure 7A:
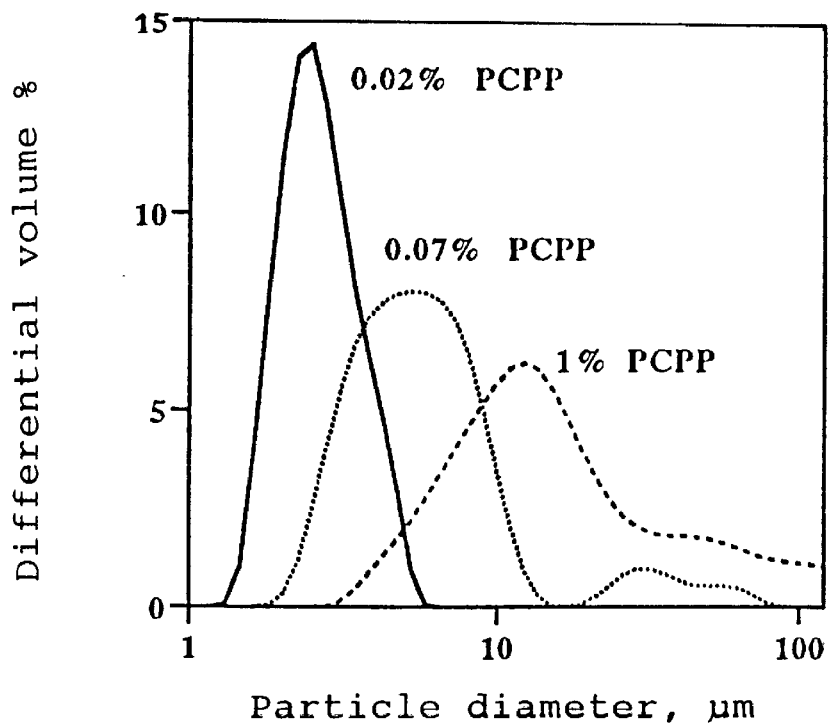
FIG. 7 is a graph of the differential percentages of microsphere diameters by volume and by number for the ionically cross-linked PCPP microspheres prepared with different concentrations of PCPP.
Figure 7B:
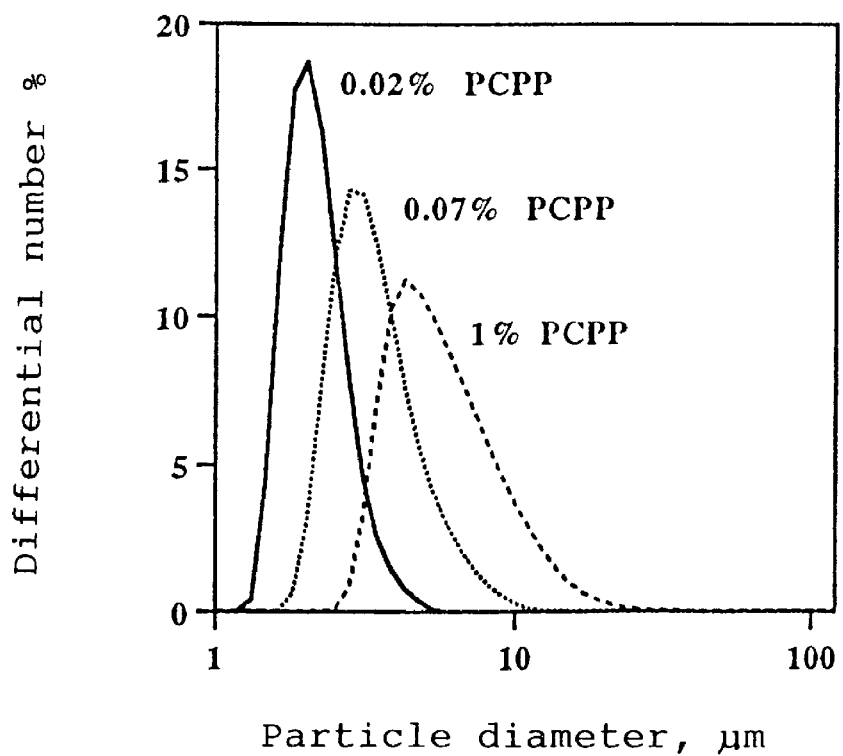

PCPP solutions with concentrations 0.07%, 0.2% and 1% were prepared and then microspheres were obtained and analyzed using the same method as in Example 3 (concentration of sodium chloride was 6.2%). As seen from FIG. 7 there was only a small increase in microsphere diameter with increase in polymer concentration.

EXAMPLE 6

Preparation of ionically cross-linked polyphosphazene microspheres containing influenza antigen.

Microspheres of PCPP containing influenza antigen were prepared by coacervating aqueous polyphosphazene—influenza antigen solution with a solution of sodium chloride in water and then by treating the resulting mixture with an aqueous solution of calcium chloride as shown in FIG. 2. 64 ml of 0.2% solution of PCPP (molecular weight—$1.1 \times 10^6$ g/mol) in PBS was mixed with 0.25 ml of solution of influenza antigen in PBS (2 mg/ml) and then 118 ml of 6.2% sodium chloride solution in water was added, shaken and incubated at room temperature for 6 minutes or until coacervate droplets with a mean size approximately 4–6 $\mu$m were formed. The coacervate dispersion was poured into 10 l of 8.8% calcium chloride solution in water. The suspension was stirred using a magnetic stirrer for 20 minutes and then microspheres were isolated by centrifugation (300 rpm, 10 min.). Microspheres were washed with deionized water and collected by centrifugation. The percentage of microspheres with size under 10 $\mu$m was 75 (by volume) and 99 (by number). The efficiency of antigen encapsulation was determined by heating microspheres in boiling water for 5 minutes and then measuring the amount of released denatured protein by gel electrophoresis. The efficiency of encapsulation was 94%.

EXAMPLE 7

Encapsulation of FITC-BSA.

5 ml of 0.2% PCPP ($M_w=1.1 \times 10^6$ mol/g) solution in PBS (pH 7.4) was mixed with 1 ml of 0.5% aqueous solution of FITC-BSA. To this solution, 9.25 ml of 6.2% NaCl was added dropwise and the mixture was shaken. After 20 min. of incubation or when the significant amount of microspheres was observed, the coacervate was poured slowly into 1 liter of 8.8% $CaCl_2$ and stirred for 10 min. The obtained microspheres were isolated as described in Example 3. Microspheres appeared as dark particles, spherical in shape and fluorescent under examination by a fluorescent microscope. Particle size analysis revealed that 90% of particles by number are smaller than 14.5 $\mu$m and 50% by volume are smaller than 9.3 $\mu$m.

EXAMPLE 8

Freeze-drying of ionically cross-linked polyphosphazene microspheres.

Microspheres were prepared by the coacervation process and isolated as described in Example 2. The microsphere suspension was then lyophilized for 32 hours and the obtained dried material was redispersed in deionized water. Particle size analysis did not reveal significant changes in microsphere size distribution.

EXAMPLE 9

Microsphere preparation using LiCl.

0.8 ml of 0.2% solution of PCPP in PBS and 1.48 ml of 40% LiCl solution in water were mixed, shaken, and incubated at room temperature for 5 minutes or until coacervate droplets with a mean size approximately 4–6 $\mu$m were formed. Then the obtained coacervate dispersion was poured in 400 ml of 8.8% calcium chloride solution in water. The microspheres were separated and their size distribution was analyzed as described in Example 3. Particle size analysis revealed that 90% of particles by number are smaller than 6.6 $\mu$m and 75% by volume are smaller than 12.4 $\mu$m.

EXAMPLE 10

Microsphere preparation using PCPP—poly (ethylene oxide—propylene oxide) interpolymer complex.

A water-soluble interpolymer complex was prepared by mixing 0.25 ml of 0.5% aqueous PCPP solution with 0.019 ml of 10% solution of poly(ethylene oxide—propylene oxide) (molar ratio 3:1, molecular weight 13,300 g/mol) in water. The obtained solution then was added to 0.1 ml of 10% NaCl solution in water and then cross-linked with 15% aqueous $CaCl_2$. Microspheres were isolated as described in Example 3 and appeared spherical in shape under examination by an optical microscope.

The disclosure of all patents, publications (including published patent applications), database accession numbers, and depository accession numbers referenced in this specification are specifically incorporated herein by reference in their entirety to the same extent as if each such individual patent, publication, database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A method of producing ionically cross-linked polyphosphazene microspheres comprising:

(a) admixing an aqueous solution containing a water-soluble polyphosphazene polyelectrolyte with a solution containing a salt of a monovalent ion to form a dispersion containing polyphosphazene coacervate microdroplets;

(b) admixing said dispersion with a solution containing a salt of multivalent ion to form a suspension of polyphosphazene microspheres.

2. The method of claim 1, and further comprising:

(c) recovering said ionically cross-linked polyphosphazene microspheres from said suspension.

3. The method of claim 1 wherein said salt of a monovalent ion is a salt of a Group I element.

4. The method of claim 3 wherein said Group I element is sodium.

5. The method of claim 4 wherein said salt of a monovalent ion is NaCl.

6. The method of claim 1 wherein said salt of a multivalent ion is a calcium salt.

7. The method of claim 6 wherein said salt of a multivalent ion is $CaCl_2$.

8. The method of claim 1 wherein said polyphosphazene polyelectrolyte is poly[di(carboxylatophenoxy) phosphazene].

9. The method of claim 1 wherein said microspheres have diameter of from about 1 to about 10 μm.

10. A method of producing ionically cross-linked polyphosphazene microspheres comprising:

(a) admixing an aqueous solution containing a water-soluble polyphosphazene polyelectrolyte with a solution containing water soluble polymer to form a water-soluble interpolymer complex of said polyphosphazene polyelectrolyte and said water-soluble polymer;

(b) admixing said interpolymer complex with a solution containing a salt of a monovalent ion to form a dispersion containing polyphosphazene coacervate microdroplets of said interpolymer complex;

(c) admixing said dispersion with a solution containing a salt of a multivalent ion to form a suspension of microspheres of said interpolymer complex.

11. The method of claim 10, and further comprising:

(d) recovering said microspheres from said suspension.

12. The method of claim 10 wherein said water-soluble polymer is poly(ethylene oxide-propylene oxide).

13. A method of producing ionically cross-linked polyphosphazene microspheres containing biological material comprising:

(a) admixing an aqueous solution containing a water-soluble polyphosphazene polyelectrolyte and biological material with a solution containing a salt of a monovalent ion to form a dispersion containing coacervate microdroplets;

(b) admixing said dispersion with a solution containing a salt of a multivalent ion to form a suspension of said ionically cross-linked polyphosphazene microsphere containing biological material.

14. The method of claim 13, and further comprising:

(c) recovering said microspheres from said suspension.

15. The method of claim 13 wherein said salt of a monovalent ion is a salt of a Group I element.

16. The method of claim 15 wherein said Group I element is sodium.

17. The method of claim 16 wherein said salt of a monovalent ion is NaCl.

18. The method of claim 13 wherein said salt of a multivalent ion is a calcium salt.

19. The method of claim 18 wherein said salt of a multivalent ion is $CaCl_2$.

20. The method of claim 13 wherein said polyphosphazene polyelectrolyte is poly[di(carboxylatophenoxy) phosphazene].

21. The method of claim 13 wherein said microspheres have diameter of from about 1 to about 10 μm.

22. The method of claim 13 wherein said biological material is selected from the group consisting of proteins, biologically active synthetic compounds, nucleic acids, and polysaccharides.

23. The method of claim 13 wherein said biological material is an antigen.

24. The method of claim 23 wherein said antigen is derived from the group consisting of rotavirus, measles virus, mumps virus, rubella virus, polio virus, hepatitis A virus, hepatitis B virus, Herpes virus, human immunodeficiency virus, influenza virus, Haemophilus influenza, Clostridium tetani, Corynebacterium diphtheria, and Neisseria gonorrhoae.

* * * * *